(12) United States Patent
Ruuska

(10) Patent No.: US 8,197,078 B2
(45) Date of Patent: Jun. 12, 2012

(54) LED LIGHT MATRIX EQUIPPED WITH IMPULSE MEANS

(75) Inventor: Hannu Ruuska, Muurame (FI)

(73) Assignee: Metso Automation Oy, Vantaa (FI)

( * ) Notice: Subject to any disclaimer, the term of this patent is extended or adjusted under 35 U.S.C. 154(b) by 232 days.

(21) Appl. No.: 12/466,436

(22) Filed: May 15, 2009

(65) Prior Publication Data

US 2009/0290323 A1 Nov. 26, 2009

(30) Foreign Application Priority Data

May 20, 2008 (FI) .................................... 20085478

(51) Int. Cl.
*G03B 15/02* (2006.01)
(52) U.S. Cl. .............................. 362/11; 362/14; 162/263
(58) Field of Classification Search .................. 362/231, 362/249.02, 249.14, 11, 253, 234; 162/263, 162/198

See application file for complete search history.

(56) References Cited

U.S. PATENT DOCUMENTS

| | | | |
|---|---|---|---|
| 1,926,292 A * | 9/1933 | Kruse ............................ | 162/198 |
| 3,922,093 A | 11/1975 | Dandliker et al. | |
| 4,882,498 A * | 11/1989 | Cochran et al. .......... | 250/559.04 |
| 6,921,182 B2 * | 7/2005 | Anderson et al. ............. | 362/231 |
| 7,186,003 B2 * | 3/2007 | Dowling et al. .............. | 362/234 |
| 7,513,651 B2 * | 4/2009 | Chen .............................. | 362/294 |
| 7,557,920 B2 * | 7/2009 | Lebens .......................... | 356/394 |
| 2004/0213016 A1 * | 10/2004 | Rice .............................. | 362/547 |
| 2005/0082027 A1 * | 4/2005 | Virtanen et al. .............. | 162/198 |
| 2006/0034085 A1 * | 2/2006 | Wang et al. ................... | 362/294 |
| 2006/0232825 A1 | 10/2006 | Freyman | |
| 2007/0144545 A1 | 6/2007 | Long et al. | |

FOREIGN PATENT DOCUMENTS

| | | |
|---|---|---|
| DE | 10117944 | 10/2002 |
| EP | 0579461 | 7/1993 |

* cited by examiner

*Primary Examiner* — John A Ward

(74) *Attorney, Agent, or Firm* — Fildes & Outland, P.C.

(57) ABSTRACT

The invention relates to a LED light matrix (14) equipped with impulse means for illuminating a moving object (10) in a selected area (11) from an oblique direction for video imaging, said LED light matrix (14) including a group of LEDs (15, 16) each equipped with optics for focusing the light produced by the LED, and with the group being located substantially obliquely relative to the object to be illuminated. Separate LEDs (15, 16) of the LED light matrix (14) are so oriented that the intensity distribution of illumination in the selected area (11) is weighted proportionally to the distance.

Figure 1:
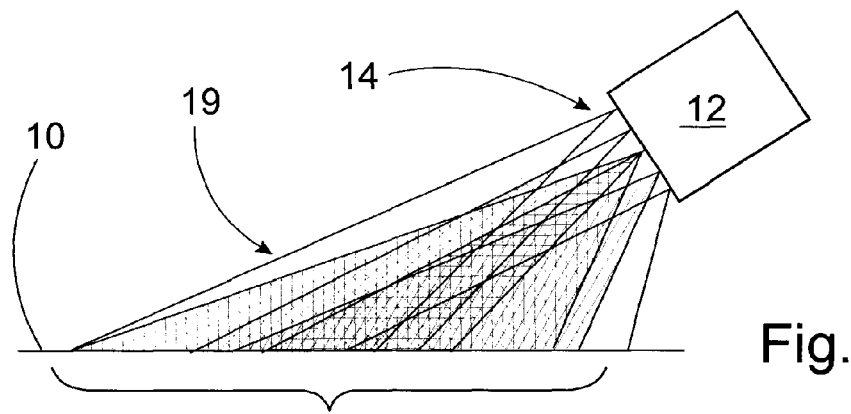

10 Claims, 4 Drawing Sheets

LED LIGHT MATRIX EQUIPPED WITH IMPULSE MEANS

BACKGROUND ART

The invention relates to a LED light matrix equipped with impulse means for illuminating a moving object in a selected area from an oblique direction for video imaging, said LED light matrix including a group of LEDs each equipped with optics for focusing the light produced by the LED, and the group being located substantially obliquely relative to the object to be illuminated.

PRIOR ART TECHNOLOGY

In particular, a paper machine has a numerous amount of objects to be monitored by video cameras where both imaging and illuminating are arranged from outside the web since imaging equipment cannot be set on top of the web. Imaging set outside the web as well as illumination always take place obliquely relative to the web. Then there is even too much light within a close range and too little light at a certain distance from the web edge. The efficiency of focused illumination reduces proportionally to the square of the distance, but the intensity of light leaving the surface of an object still decreases to the third power. The effective imaging area remains rather small and often the image cannot be extended even near to the machine center point.

Imaging of a quickly moving web or object with a LED stroboscope light is known, for example, from publications WO 2007/096475, WO 2004/063664 and U.S. Pat. No. 5,936,353, as well as from Finnish patent application 20065570.

Still commonly used in the paper machine environment are halogen lights and metal halide lights, which have high power consumption, whereby the heat generation is also problematically great. Hot lamps can even cause a fire when waste accumulates on top of the lamp. However, so far the use of LED light matrices has been rather limited, although they reduce substantially the power consumption and heat generation. The luminous efficiencies of LEDs have already increased so that they are worthy as a light source for video monitoring. In any case, an oblique illumination angle is an obvious problem also when using LED light fixtures. With increasing illumination efficiency, their glare effect usually increases, which impairs working conditions.

SUMMARY OF INVENTION

The objective of this invention is to provide an improvement in imaging conditions and even to enable imaging further within the machine. The characteristic features of the LED light matrix according to this invention are set forth in the appended claim 1. The efficiency of a LED light unit when provided with impulses remains a fraction compared to a halogen lamp with a corresponding efficiency; thus the fire risk is eliminated. In an advantageous embodiment, at least part of the LEDs emit monochromatic light the color of which has been selected according to the object to be illuminated. In many cases, a green color is advantageous for white paper and white is advantageous for brown paper.

In one application at least two types, as for the radiation beam, of LED components with respective optics are used, i.e. separate lenses of two or more types are generally used with similar LEDs to create different beams. The matrix can always be assembled from these beam types in such a way that an intensity distribution that is emphasized at the furthest end is achieved. The intensity varies in the selected illuminated area according to a coefficient which is in a range of 2-10. In practice, a near edge thus receives light only a fraction compared to a selected furthest point.

In one application the LEDs of the matrix are oriented in either one or more planes for achieving a desired intensity distribution. In other words, the matrix has curvature in either one or two planes. Alternatively, the light fixture can be assembled from more than one matrix each of which can be equipped with desired illumination beams and each can be separately oriented to the area to be illuminated for creating an optimum imaging area illumination. At the same time, it is also possible to use LEDs with different beams. A useful method is to divide the matrix into bands which are separately oriented.

In one advantageous application, the imaging area, and hence the illuminated area, is a rectangular where the ratio of the longer side relative to the shorter side is within a range of 1.25-5. The illuminated area corresponds at least to the imaging area of the camera but it can also be emphasized only to the illumination of the object to be imaged, which area can have a different shape compared to the imaging area of the camera.

A LED light matrix is advantageously located in a camera casing, which avoids a separate unit with the respective auxiliary functions (e.g. cleaning). A LED light matrix can also be located in a separate light fixture casing, in which case it can be utilized for improving the illumination of already existing cameras. Similarly, when using very high efficiencies, the LED surface area can grow so large that the use of a separate light fixture casing is justifiable.

The other advantages and embodiments of the invention are described below.

DETAILED DESCRIPTION OF INVENTION

The invention is described below by means of examples and enclosed drawings.

Figure 2:
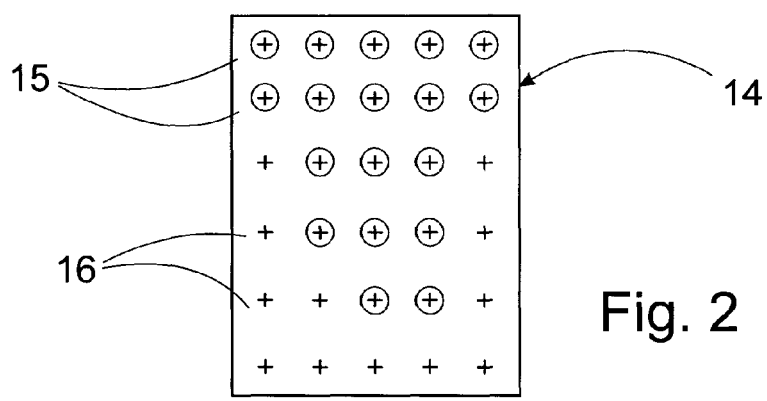
Figure 3A:
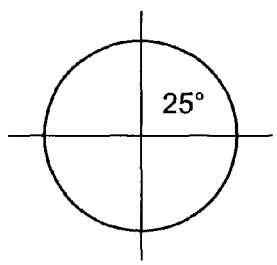
Figure 3B:
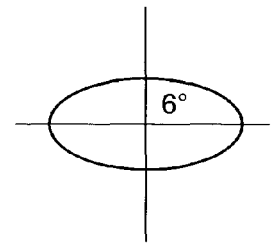
Figure 3C:
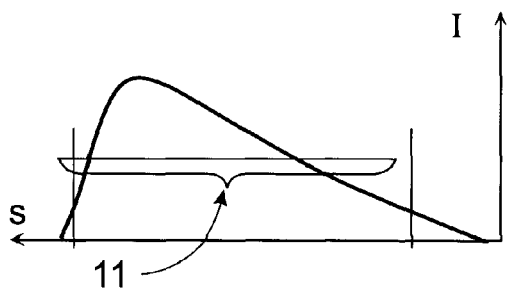
Figure 4:
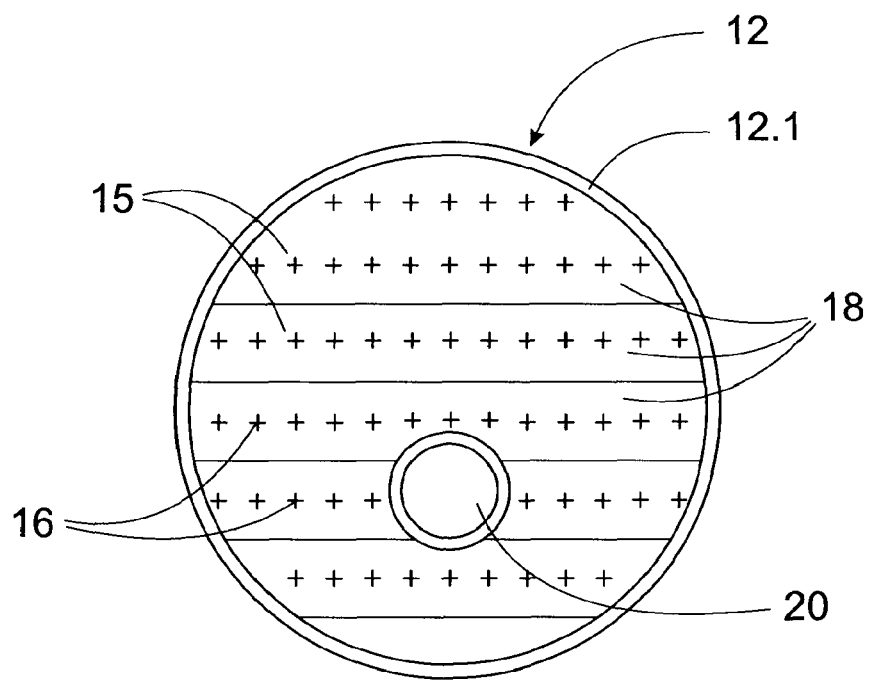
Figure 5:
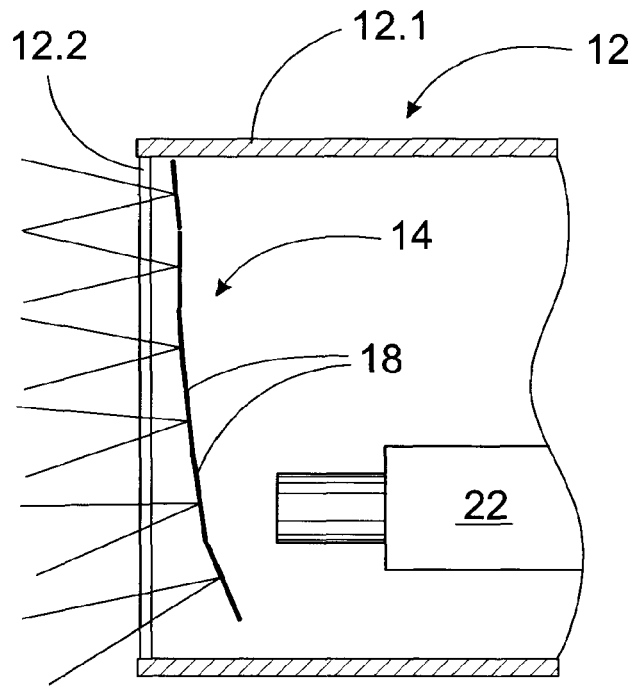
Figure 6:
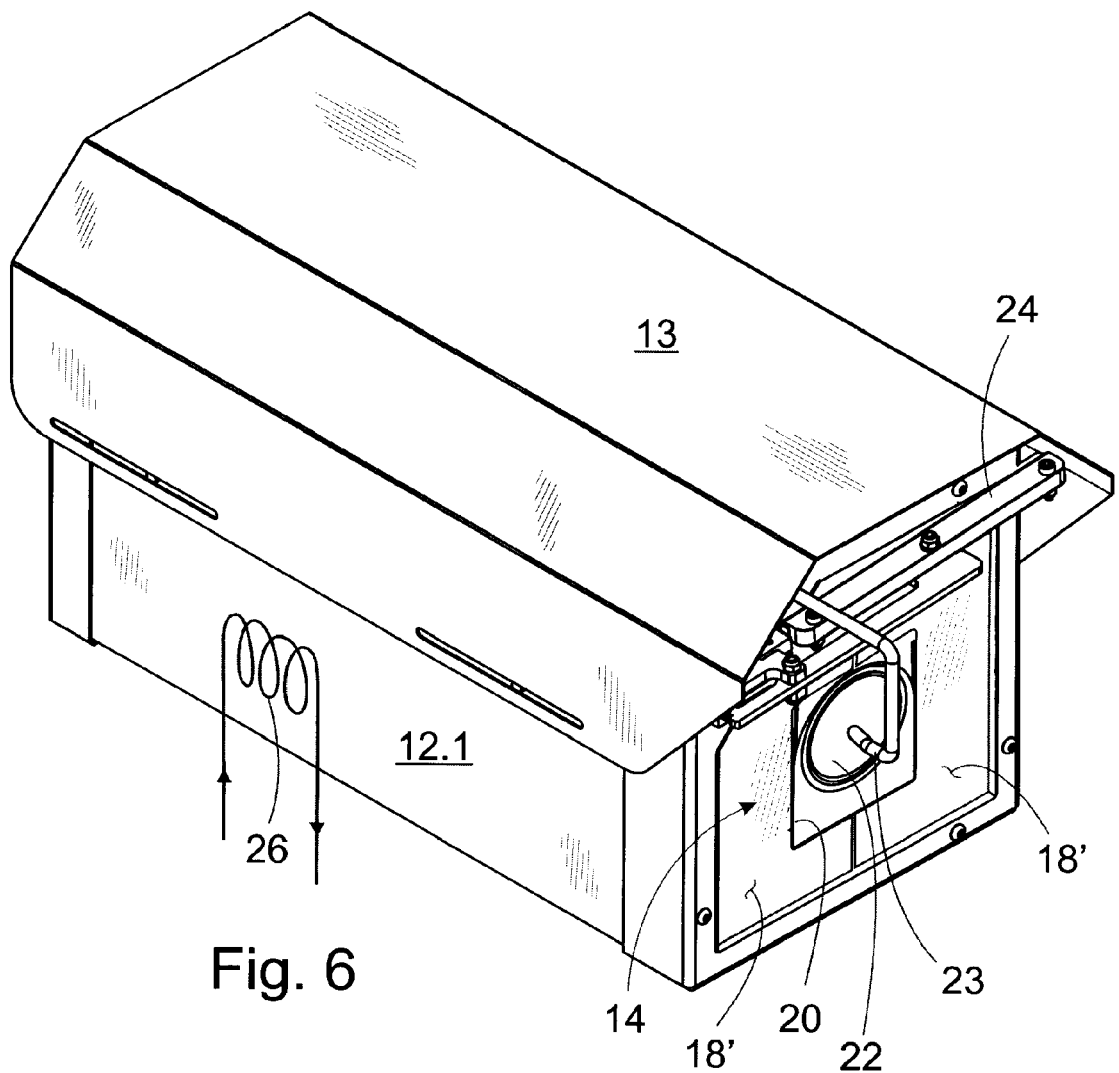
Figure 8:
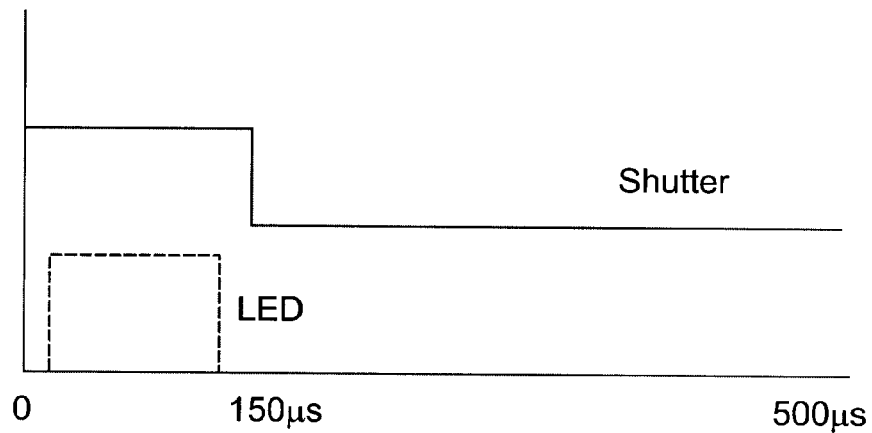
Figure 7:
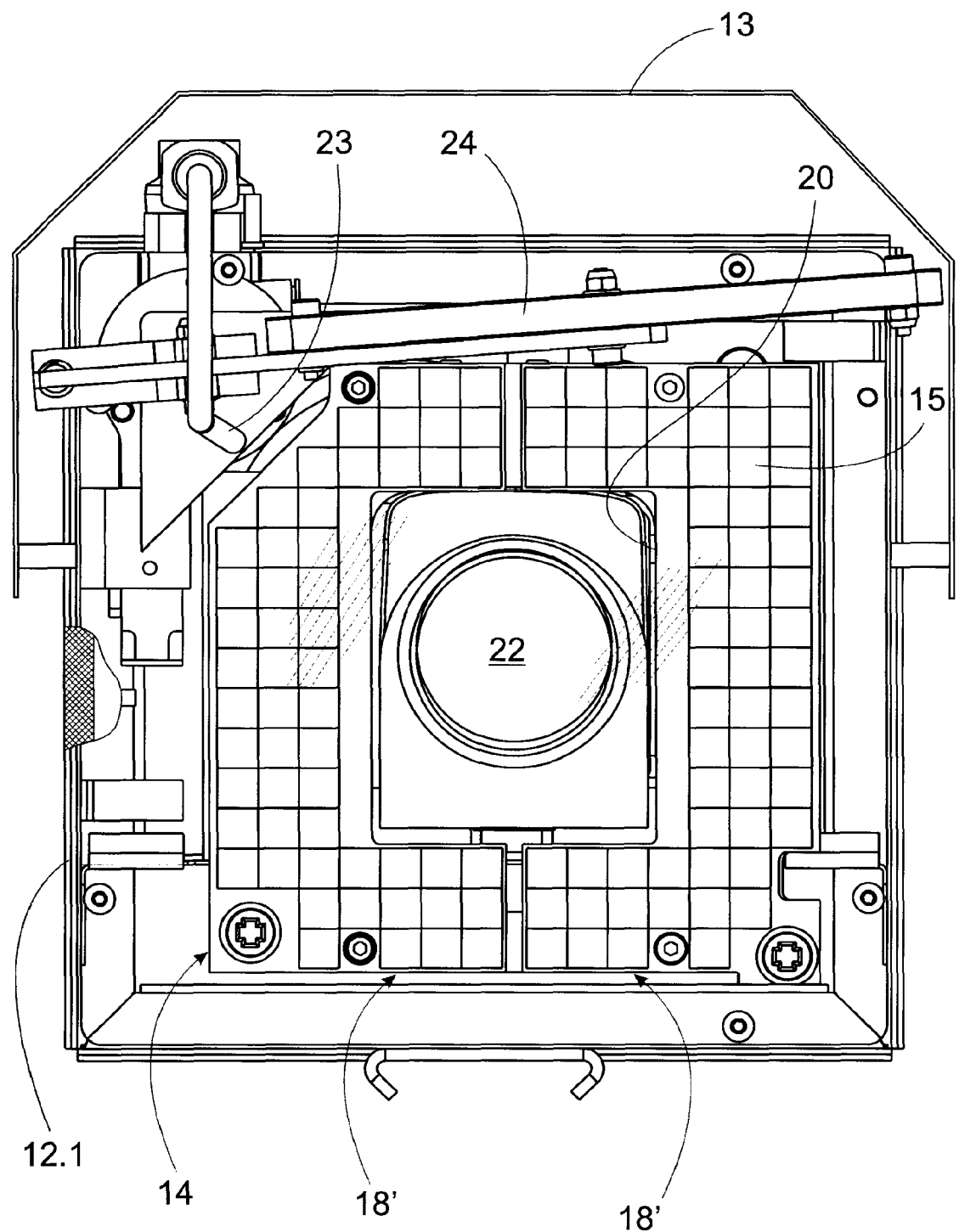

FIG. 1 is a side view of an illumination geometry,

FIG. 2 is a schematic view of a LED light matrix according to the invention, FIGS. 3a and 3b illustrate two different types of radiation beams, FIG. 3c illustrates the intensity distribution of illumination in a selected area, FIG. 4 is a front view of a camera illumination unit, FIG. 5 is a lateral cut view of the unit of FIG. 4, FIG. 6 is an axonometric view of another camera illumination unit, FIG. 7 is a direct front view of the unit of FIG. 7, FIG. 8 illustrates the mutual timing of a camera shutter and a LED light impulse.

In the example of FIG. 1, a light matrix 14 in a light unit 12 illuminates an object 10 (a paper machine web, for example) in a selected area 11. The web travels orthogonally to the imaging plane the selected area 11 being thus a narrow band extending from the web edge toward the center. The length of the impulses is 10-500 µs being always substantially shorter than the camera's shutter speed and the impulses are adapted to correspond to a distance of 1-5 mm, advantageously of 1-2 mm, at the web speed concerned. (At a speed of 1200 m/min, or 20 m/s, the web travels 2 mm in 100 µs.) The impulses are accurately timed to operate while the camera shutter is open, or the common time is accurately regulated in some other way. It is advantageous to time the impulse completely for the time of the shutter's open position (FIG. 8), which allows utilizing fully the light impulse. In addition, opening and closing of an electronic shutter are usually sliding events over an image matrix.

In FIG. 2, the light matrix 14 comprises LEDs 15, 16 with lenses in six rows. The circled LEDs 15 are LEDs with narrow beams and the other ones are LEDs 16 with wide beams. With this arrangement, too, a better intensity distribution than before can be achieved for the selected area. High-efficiency LEDs, efficiency class 6 W (April 2009), are used here, but such that can be momentarily loaded by means of pulsing with a notably higher efficiency. One LED supplier is Philips (NL) and one trademark is Luxeon®, for example type K2 1000 mA—cool white LXK2_PW14_T00 or LXML_PWC1_0100. Lenses are used on top of the LEDs to focus the light in a desired beam, for example the following: the oval lens is Carclo 10415 (Carclo Technical Plastics, GB) and the spot lens is Carclo 10412. Another alternative is LEDIL OY(FI) "CRS SQUARE lenses for CREE XR/-E LEDs".

FIGS. 3a and 3b show the illumination area of a wide-beam and a narrow-beam LED in an orthogonal plane. Optics related to the LED enables different radiation beams which can have directivity in either one or two dimensions.

According to FIG. 3c, the intensity distribution is asymmetric in the selected area 11. Illumination intensity increases from the web edge up to the other end. For a camera sensor, the intensity is constant in an ideal case, but it is naturally sufficient that the variation is clearly within the sensor dynamics.

The light matrix 14 can naturally be implemented as a separate unit, which is also sometimes necessary, but advantageously it is integrated to a camera unit 12. This includes common auxiliary equipment, for example, cooling elements and glass cleaning means (not shown). Thus the light matrix 14 is fitted to a camera casing 12.1 having a glass plate 12.2 at its end. The camera 22 images through an aperture 20 left in the matrix, FIG. 4. The aperture 20 is arranged asymmetrically, which allows obtaining proportionally more LEDs that are naturally oriented distantly, than LEDs that are oriented to a near distance.

The matrix comprises several discrete strips 18, which are circuit boards supporting the LEDs. These strips 18 form a curve that curves down increasingly steeply, FIG. 5. At the other end, one or more strips can be slightly bent to the opposite direction for focusing the radiation optimally.

Advantageously, the LEDs emit a green light which has a great difference of sensibility between the human eye and the camera sensor. The LEDs are controlled in a known way by an impulse oscillator which is synchronized with the camera.

The LED light matrix 14 includes advantageously 100-300 LEDs 15, 16.

In the application example of FIGS. 6 and 7, the LED light in the camera casing uses 117 LEDs a 6 W (nominal efficiency 3 W), i.e. a total efficiency of 712 W. The dimensions of the light fixture are 200×200×300 (L) mm. Functionally similar parts are referred to using the same reference numbers as above. Here the light fixture is also integrated to a camera unit 12 located in a thermally insulated casing 12.1 provided with cooling, which is indicated schematically with reference number 26. Simple compressed air cooling is sufficient up to an environmental temperature of 60° C. and a vortex cooler is used in hotter conditions (up to 115° C.). Despite the high nominal efficiency of the LED light fixture, its continuous efficiency is only 30 W. Like in FIG. 5, the light matrix 14 is here integrated to the camera unit 12, which includes shared cooling elements 26 and glass cleaning means, such as a wiper 24 and a cleaning water supply 23. At the end of the camera casing 12.1, this application also has a glass plate 12.2 which covers the two-part light matrix 14. The camera 22 images through an aperture 20 left in the light matrix 14. The camera casing 12.1 has a splash guard 12 on top and its wall is provided with PU insulation 27, FIG. 7.

The parts 18' and 18" of the light matrix 14 are orientable, i.e. the matrix has two halves which can be individually oriented to a desired direction (thus this corresponds to a curved construction). In addition, LED matrices can be fitted with horizontal, vertical and spot lenses. For example, the left matrix part 18' is equipped with spot lenses and oriented to the web edge. On the right-hand side, the matrix part 18" uses a vertical lens on top of each LED, which is oriented to the direction of a roll (thus this corresponds to wide-beam and directional optics). The casing 12.1 can be turned by 90° and simultaneously the camera is turned inside to the opposite direction so that the image remains constant but the directionability of the light matrix 14 changes vertical. In this way the matrix halves can be oriented also in the up/down direction in case the camera position requires it.

A separate LED light fixture has a total of 3 elements of 63 LEDs each of which provides an impulse efficiency of 380 W with the actual power consumption being only 10 W. The elements are separately oriented as above and they are equipped with desired optics.

It is essential for a LED light fixture according to the invention that it includes synchronization means which are connected to the camera shutter.

The invention claimed is:

1. An arrangement for illuminating and imaging a paper machine moving web having a near edge, the arrangement comprising:
   a camera with a sensor having dynamics for video imaging of the web; and
   an illumination unit having impulse means and a LED light matrix for illuminating the web in a selected area from an inclined direction for video imaging;
   the LED matrix including LEDs and optics for focusing the light produced by each LED, each LED being oriented so that the intensity of the illumination increases from the near web edge up to another end of the selected area to radiate the selected area with an asymmetric intensity distribution, and the variation of intensity sensed by said sensor of the camera is within sensor dynamics;
   wherein both the camera and the LED light matrix are arranged outside the web, and the LED light matrix illuminates the web obliquely.

2. An arrangement according to claim 1, wherein the LEDs of the LED light matrix with the respective optics are at least of two types as for their directional pattern comprising narrow-beam and wide-beam types, and the LEDs are divided to the matrix based on their beam type so that the number of narrow-beam LEDs is the greater, the further away the LED is located from the moving web.

3. An arrangement according to claim 1, wherein the LED matrix is so designed as a group that illumination is focused, relative to the distance, more to a far distance than to a near distance.

4. An arrangement according to claim 3, wherein the LED matrix has a curved cross-section with the curvature increasing toward the end that illuminates the near region.

5. An arrangement according to claim 4, wherein the LED light matrix is divided into several discrete parts, these parts roughly forming said curvature.

6. An arrangement according claim 1, wherein the selected area illuminated by the LED light matrix is rectangular where the ratio of the longer side relative to the shorter side is within a range of 1.25-5.

7. An arrangement according to claim 1, wherein the intensity of illumination produced by the LED light matrix varies proportionally within a selected range relative to the distance of a point illuminated by a coefficient of 2-10.

8. An arrangement according to claim 1, wherein the LED light matrix includes 100-300 LEDs divided into at least two elements that are separately orientable.

9. An arrangement according to claim 1, wherein the LED light matrix is integrated to a camera casing and an imaging aperture is asymmetrically located at the center of the LED light matrix.

10. An arrangement according to claim 1, wherein at least part of the LEDs emit monochromatic light the color of which is selected according to the moving web.

* * * * *